United States Patent [19]

Karnicky et al.

[11] Patent Number: 4,582,654
[45] Date of Patent: Apr. 15, 1986

[54] NEBULIZER PARTICULARLY ADAPTED FOR ANALYTICAL PURPOSES

[75] Inventors: Joseph F. Karnicky, Menlo Park; Louis T. Zitelli, Palo Alto, both of Calif.

[73] Assignee: Varian Associates, Inc., Palo Alto, Calif.

[21] Appl. No.: 649,585

[22] Filed: Sep. 12, 1984

[51] Int. Cl.[4] .............................................. B05B 17/06

[52] U.S. Cl. ...................................... 261/81; 239/102; 261/DIG. 48

[58] Field of Search ......................... 261/DIG. 48, 81; 239/102, 4

[56] References Cited

U.S. PATENT DOCUMENTS

| | | | |
|---|---|---|---|
| 2,163,649 | 6/1939 | Weaver | 261/DIG. 48 |
| 2,532,554 | 12/1950 | Joeck | 239/4 |
| 3,392,916 | 7/1968 | Engstrom et al. | 261/DIG. 48 |
| 3,729,138 | 4/1973 | Tysk | 261/DIG. 48 |
| 3,866,831 | 2/1975 | Denton | 239/102 |
| 4,109,863 | 8/1978 | Olson et al. | 261/DIG. 48 |
| 4,190,203 | 2/1980 | Hughes | 261/DIG. 48 |
| 4,319,155 | 3/1982 | Nakai et al. | 239/102 |
| 4,336,509 | 6/1982 | Bernitz | 239/102 |

FOREIGN PATENT DOCUMENTS

| | | | |
|---|---|---|---|
| 26041 | 11/1963 | German Democratic Rep. | 293/102 |
| 56-34943 | 7/1981 | Japan | 261/DIG. 48 |

*Primary Examiner*—Tim Miles

*Attorney, Agent, or Firm*—Stanley Z. Cole; Peter J. Sgarbossa

[57] ABSTRACT

A nebulizer for analytical purposes includes a needle through which flows a liquid to be nebulized. The liquid flows from the needle onto a diaphragm planar surface that is vibrated in successive pulses. A continuous bridge of the liquid subsists between the liquid and the planar surface when the diaphragm is in the non-vibrating state. The liquid is nebulized to an aerosol when the diaphragm is pulsed. The needle and diaphragm are always spaced from each other. A wick on the planar surface in contact with the film removes excess amounts of the liquid not involved in forming the aerosol. The diaphragm vibration is pulsed by a piezoelectric crystal that responds to an FM wave whose frequency is swept over a band spanning the resonant frequency of the crystal. The crystal is configured as a spherical segment to direct a focused pressure wave on the diaphragm via a liquid medium. The diaphragm has a thickness that is about one-half wave length of the pressure wave supplied to the liquid medium by the crystal, to provide destructive interference of waves reflected from opposite faces of the diaphragm. A carrier gas for the nebulized aerosol is supplied to the diaphragm planar face to form a curtain about the liquid flowing from the needle to the diaphragm. The liquid circulates between the diaphragm and crystal to cool them and enable gases in the liquid to be removed.

23 Claims, 3 Drawing Figures

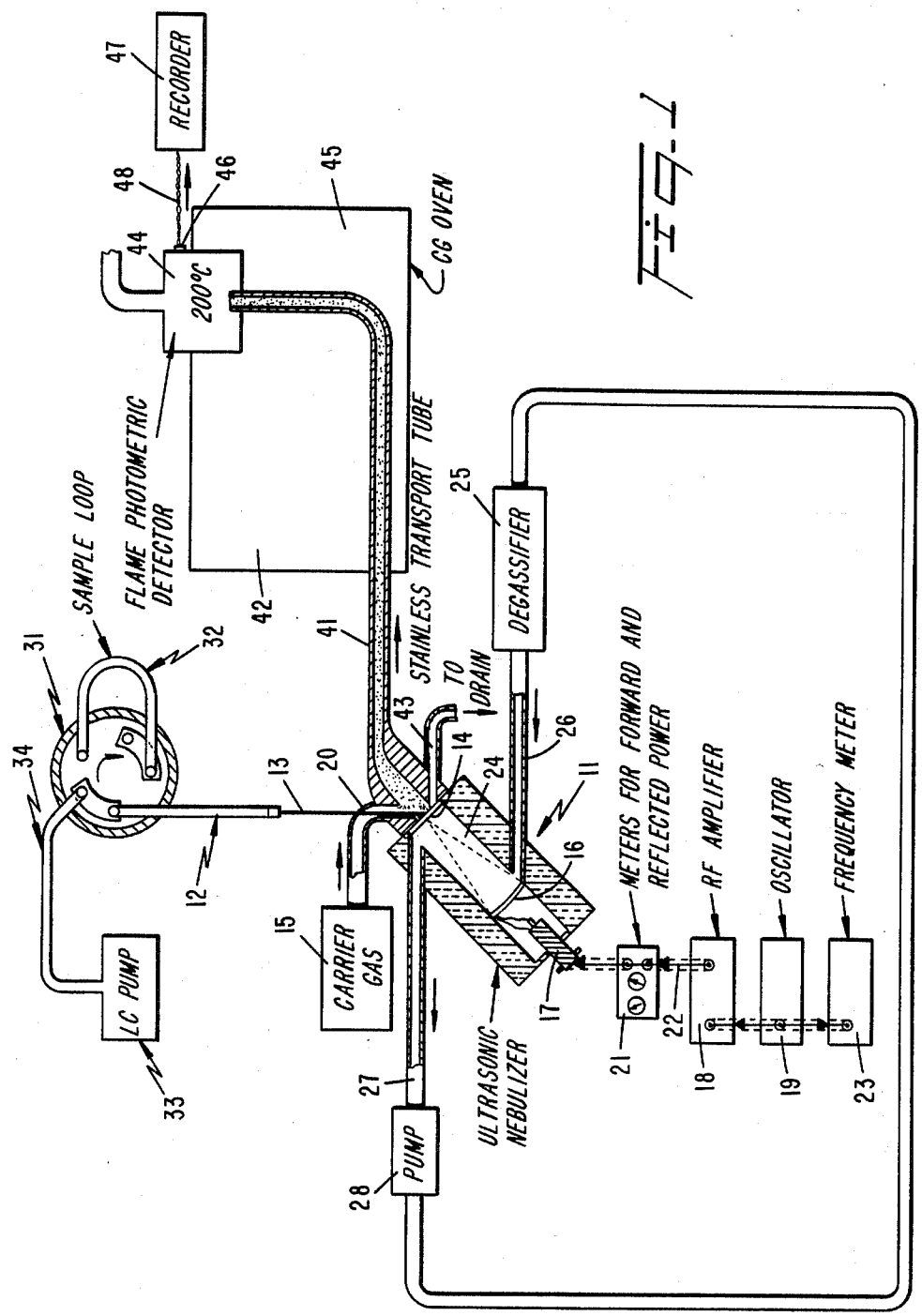

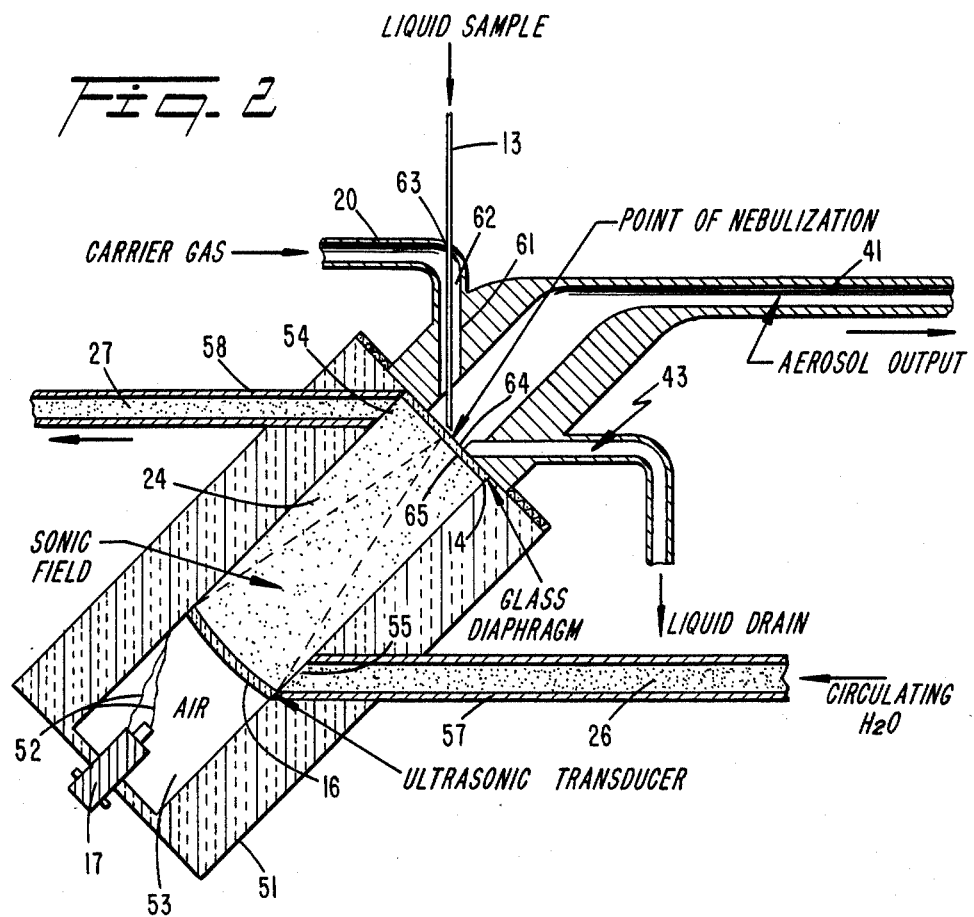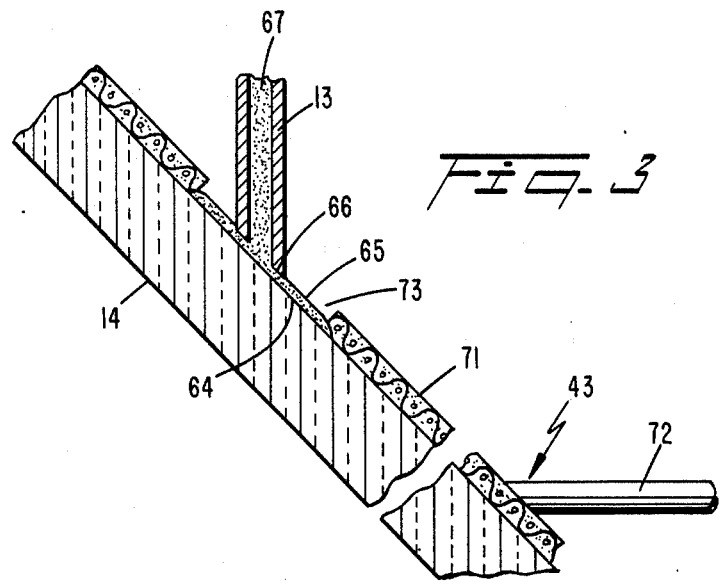

NEBULIZER PARTICULARLY ADAPTED FOR ANALYTICAL PURPOSES

TECHNICAL FIELD

The present invention relates generally to nebulizers and more particularly to a nebulizer particularly adapted to be used in connection with analytic devices.

BACKGROUND ART

Nebulizers for analytical purposes are known in the art; see for example the papers by Denton, et al, Analytical Chemistry, Volume 44, February 1972, pp 241 ff; by Chester, Analytical Chemistry, Volume 52, September 1980, pp 638 ff and 1621 ff; Denton, U.S. Pat. No. 3,866,831; Olson, et al, U.S. Pat. No. 4,109,863; and Smith, Jr., et al, U.S. Pat. No. 4,361,401. Such nebulizers convert a liquid, for example, a liquid chromatography effluent, into an aerosol that is supplied to a gas-type detector, such as a flame photometric detector. One general prior art type of nebulizer is characterized as a pneumatic nebulizer wherein a liquid to be nebulized is shattered into droplets by supersonic gas flowing through an orifice. The orifice may be of the Venturi-type wherein liquid is sucked into a nubulizing region by a Bernoulli effect. Alternatively, the orifice can be of the Babbington-type wherein liquid is pumped across a nebulizing orifice. Another prior art nebulizer is an ultrasonic bath nebulizer wherein a volume of liquid is maintained in the nebulizer and nebulization occurs from the liquid surface. An additional prior art nebulizer is characterized as a flow nebulizer wherein a liquid flows onto a vibrating surface. A further type of prior art nebulizer includes a single droplet generator wherein the liquid to be nebulized is pumped through a vibrating capillary tube. The flow nebulizers are generally characterized by metal longitudinal or flexing oscillators or a glass surface covering a piezoelectric crystal, such as disclosed by Olson et al, or a glass or plastic diaphragm activated by coupling ultrasonic excitation through a liquid medium.

Pneumatic nebulizers, as contrasted to ultrasonic nebulizers, produce aerosols containing a wide range of droplet sizes; some of the droplets have a relatively large diameter. Pneumatic nebulizers work well with relatively high gas and liquid flows on the order of 10 liters per minute of gas and one cubic centimeter per minute of liquid. The typical gas analyzer is incapable of adequately handling an aerosol resulting from this nebulization. The pneumatic nebulizers exhibit severe problems in manufacture and alignment if attempts are made to design them to provide gas flow rates to an analyzer of less than one liter per minute. The efficiency of aerosol production by pneumatic nebulizers is relatively low and the resultant mist has a low droplet density.

Bath-type ultrasonic nebulizers have a relatively large volume of in-transit liquid, which results in unacceptable loss of resolution of the output of a liquid chromatography column or flow injection analyzer. The unacceptable loss of resolution or band broadening occurs for liquid flow rates of less than or equal to approximately 1 cubic centimeter per minute.

Ultrasonic nebulizers having flat crystals consume relatively large amounts of power, approximately 50 watts. This is undesirable because of the necessity to provide relatively expensive, complex and difficult to design amplifiers for radio frequency sources required to drive the piezoelectric crystal of such nebulizers. In the typical prior-art flat crystal ultrasonic nebulizer, the minimum achievable mixing volume is the volume of one liquid drop before nebulization, i.e., about 20 microliters. On the other hand, metallic resonators exhibit mechanical problems at frequencies above 100 KHz. Because drop size is related to oscillation frequency, with increasing frequency resulting in decreased drop size, such devices produce drops that are excessively large for many gas analyzers; the diameter of such drops is typically on the order of 50 microns.

Single droplet generators also produce aerosol drops having relatively large diameter and thus are incompatible with many gas analyzers. In addition, single droplet generators employ capillary tubes which are subject to plugging and therefore require extensive maintenance.

It is desirable in many analytical systems for a nebulizer to produce a dense aerosol of small, uniformly sized droplets from a liquid flowing at rates from 10 to 200 microliters per minute, as derived from a liquid chromatography column. The small, uniformly sized droplets must be capable of being mixed with a carrier gas having a flow rate as low as 30 cubic centimeters per minute. It is preferable for the nebulizer mixing volume to be on the order of 1 microliter so that the nebulizer can be used for supplying an aerosol from the effluent of a micro liquid chromatography column; such columns typically have an inner diameter of 1 millimeter. The low carrier gas flow, combined with a variable efficiency for the nebulizer, enables the aerosol to be supplied to a typical gas chromatography detector, such as a flame photometric detector, a flame ionization detector, or a mass spectrometer ion source. To minimize cost of the nebulizer, it is desirable for RF power supplied to a crystal to be minimized to a few watts. This enables amplifiers for supplying such power to be relatively low cost, and simple structures.

A further problem with prior nebulizers employing electric wave to pressure-wave transducers, e.g., piezoelectric crystals, is that such transducers have a tendency to change resonant frequency characteristics as a function of ambient conditions. In particular, as temperature changes, the resonant frequency of a piezoelectric crystal changes.

DISCLOSURE OF INVENTION

The nebulizer of the present invention forms an aerosol from liquid flowing through the interior bore of a hollow needle. The supplied liquid in the bore flows from the open end of the needle onto a diaphragm having a planar surface. The diaphragm is activated to cause the planar surface to oscillate at high frequency in a direction normal to the planar surface. This oscillation is pulsed repetitively at low frequency.

To achieve the small mixing volume that enables proper operation with analyzing devices with which the present invention is desired to be used, the diaphragm is positioned relative to the needle opening so that a continuous bridge of the liquid subsists between liquid inside the bore and the planar face. The bridge is part of a liquid film on the planar surface. The liquid in the film is nebulized to an aerosol that flows away generally at right angles from the planar surface in response to the diaphragm oscillation. The diaphragm and needle are positioned so that the diaphragm and needle are always spaced from each other, to avoid damage to the diaphragm and/or needle.

To assist in maintaining the film on the planar surface and keeping the bridge intact, the planar surface is maintained at a substantial angle from the vertical and the horizontal so that the excess liquid can be drained from the planar surface. Preferably, the inclination angle of the planar face is 45° from the vertical.

To facilitate flow of liquid onto the planar face, the needle is vertically oriented. To assist in achieving the film bridge, the tip of the needle is beveled at the same angle which subsists between the planar surface and the bore of the needle so there is a substantially uniform gap between the needle tip and the planar surface. To achieve a mixing volume on the order of 1-2 microliters, the gap between the needle and the planar surface is approximately 0.002 inches and the bore has a diameter of approximately 0.006 inches.

To assist in removing the excess liquid from the planar surface, a wick on the planar surface contacts the film. Removal of excess liquid is necessary because a maximum of 30% of the liquid supplied by the needle to the planar face is nebulized. The wick includes a generally planar screen segment overlaying a portion of the planar surface of the diaphragm and a central cut-out region into which the needle extends where the film and bridge subsists. The wick includes a cord portion contacting the screen segment for drawing liquid in the screen segment away from the planar diaphragm surface.

The activator for moving the diaphragm in a pulsed vibrational manner includes a resonant transducer of electric wave to pressure wave, preferably a piezoelectric crystal. Such transducers have a tendency to change resonant frequency as a function of ambient conditions. In particular, the resonant frequency of a piezoelectric crystal changes as a function of temperature. In the past, relatively expensive and in many instances difficult temperature compensation circuits have been employed to drive a piezoelectric crystal into oscillation at the desired resonant frequency thereof.

In the present invention, the need for such compensating circuits is obviated and the pulsing is achieved by applying a swept frequency-modulated electric wave to the transducer. One of the frequencies in a band through which the electric wave is swept causes the transducer to be activated in the resonant condition for the ambient conditions of the transducer. Activation of the transducer at its resonant frequency causes the diaphragm to oscillate at that frequency during the time the frequency of the applied RF driving power is near the crystal's resonant frequency.

We have discovered that the low-frequency modulating on-and-off of the diaphragm's high-frequency vibration has unexpected importance for operation of the nebulizer. If the vibration is not pulsed, the smooth bridge of liquid on the diaphragm surface breaks up and the aerosol particles are not produced in the desired uniform, small size.

It should be noted that, with the swept-frequency modulation, the crystal vibration does not reduce to zero off resonance. The crystal vibrates a little in response to frequencies other than its resonant frequency, but the amplitude is very small and for practical purposes may be considered zero. At least it is small enough for the liquid film to be maintained.

The resonant frequency of piezoelectric crystals utilized as electric wave pressure wave transducers is a function of the crystal thickness. The drop size of the liquid particles of the aerosol established by the nebulizer is a function of the frequency of the pressure wave incident on the diaphragm which determines the diaphragm oscillation frequency. As the diaphragm oscillation frequency increases, the aerosol drop diameter decreases. Piezoelectric crystals having a thickness necessary to achieve the desired aerosol drop diameter, e.g., 4 microns, have such narrow thicknesses as to be mechanically unstable and have a tendency easily to break.

To provide a piezoelectric crystal having the desired mechanical properties and to activate the diaphragm with a high enough frequency, e.g., approximately 3 MHz, to achieve the desired small diameter aerosol, the crystal is selected to have a fundamental resonant frequency that is a sub-harmonic of the operating frequency, i.e., the frequency which drives the diaphragm. In the specific embodiment, the fundamental crystal resonant frequency is one-third of the diaphragm activation frequency. The crystal oscillates in a third-harmonic mode.

To minimize the power necessary to drive the transducer and thereby obviate the requirement for a relatively high power, expensive and complex RF amplifier responsive to a low power RF source, the pressure wave is very efficiently coupled between the pressure wave source, i.e., the crystal, and the diaphragm. In particular, the pressure wave source is positioned remotely from the diaphragm and is configured to direct a focused pressure wave on the diaphragm by way of a fluid medium located between the pressure wave source and diaphragm. In the preferred embodiment, the focused pressure source is a crystal shaped as a sector of a sphere having a concave surface from which the focused wave is derived. To maximize the efficiency, the tendency for destructive interference due to pressure waves reflected from the opposed faces of the diaphragm is substantially eliminated by designing the thickness of the diaphragm so that it is approximately one-half wave length of the wave frequency propagating through the diaphragm. The diaphragm is thus mechanically resonant in the half-wave mode of the pressure wave.

The pressure wave coupled from the pressure wave source to the diaphragm propagates through a fluid medium, preferably a liquid that is circulated in a chamber between the pressure wave source and the diaphragm. The circulating liquid medium cools the diaphragm and the pressure wave source. The circulated liquid also passes through a degassifier so that any bubbles formed in liquid resident in the chamber are substantially eliminated. Bubbles in the chamber could have the adverse effect of defocusing the pressure wave propagating between the pressure wave source and the diaphragm. This is because the pressure wave propagates at a different velocity in a gaseous medium compared to a liquid medium, thus the wave is bent as it propagates between liquid and gaseous mediums.

To assist in providing maximum transfer of the nebulized liquid to an analyzer, a carrier gas for the nebulized aerosol is supplied to the planar face so that it surrounds the needle. To this end, the carrier gas supply includes a tube having an opening through which the needle extends. The carrier gas flows through the tube toward the planar diaphragm surface so that the gas forms a curtain about the liquid flowing from the needle to the diaphragm planar face. The carrier gas may be the diverted flow of one of the gas supplies normally fed to the detector.

The above and still further objects, features and advantages of the present invention will become apparent upon consideration of the following detailed description of one specific embodiment thereof, especially when taken in conjunction with the accompanying drawings.

BRIEF DESCRIPTION OF DRAWINGS

FIG. 1 is a schematic block-like diagram of a liquid chromatography unit in combination with a flame photometric detector and a nebulizer in accordance with the present invention;

FIG. 2 is a schematic diagram of a side view of a micro-nebulizer in accordance with a preferred embodiment of the invention; and FIG. 3 is an enlarged side view of a micro-nebulizer in accordance with the invention wherein a wick is illustrated as surrounding a film on a planar surface of the diaphragm.

BEST MODE FOR CARRYING OUT THE INVENTION

Reference is now made to FIG. 1 of the drawing wherein ultrasonic nebulizer 11 is illustrated as being responsive to a liquid derived from the output of liquid chromatography column 12, which is preferably a so-called micro liquid chromatography column. Chromatography column 12 typically has eluting peaks between four microliters and 30 microliters. The output of liquid chromatography column 12 is supplied via a needle 13 to a pulsed oscillation diaphragm 14 of nebulizer 11. Because of the low flow rate of liquid supplied by needle 13 to diaphragm 14, nebulizer 11 can be considered as a micro-nebulizer. Diaphragm 14 is flooded by a carrier gas derived from carrier gas source 15, typically a compressed air source. In a preferred embodiment, the carrier gas is supplied to diaphragm 14 by conduit 20 and source 15 at a rate of 30–200 cubic centimeters per minute. Diaphragm 14 is driven in ultrasonic oscillation by a piezoelectric crystal 16 at an RF frequency, such as 3.36 MHz.

Crystal 16 is electrically driven by electrodes (not shown) connected to the output of RF amplifier 18 via coaxial connector 17. Amplifier 18 is driven by the RF output of signal generator 19. To monitor the power coupled by amplifier 18 to crystal 16 and the power reflected by the crystal back to the amplifier, meter network 21 is connected in series with cable 22 that couples the RF signal from amplifier 18 to connector 17. The output frequency of signal generator 19 is monitored by frequency meter 23.

Crystal 16 is an electric-to-pressure wave transducer having a tendency to change resonant frequency as a function of ambient conditions; in particular as a function of ambient temperature. To enable crystal 16 to be driven periodically at the resonant frequency thereof, without the need for temperature compensating circuits, the frequency of signal generator 19 is swept through a range of frequencies, spanning the resonant frequency of crystal 16 for the particular ambient temperature being experienced by the crystal. Sweeping of the frequency of signal generator 19 occurs at a rate in the range of 10 to 100 sweeps per second, i.e., a 10 to 100 Hertz rate. Each time signal generator 19 goes through the resonant frequency of crystal 16 or the utilized harmonic thereof, the crystal is activated to supply a pressure wave at the resonant frequency or harmonic thereof to diaphragm 14.

To minimize the tendency for crystal 16 to break and enable the crystal to be relatively thick while supplying relatively high frequency pressure waves, such as 3.36 Mhz, to diaphragm 14, the output frequency of generator 19 is a harmonic of the fundamental resonant frequency of crystal 16. Typically the output of generator 19 is at the third harmonic resonance of crystal 16 so that for a pressure wave of 3.36 MHz, crystal 16 is resonant at 1.12 MHz and source 19 generates a 3.36 MHz sinusoidal wave. The output frequency of generator 19 is swept through $\pm 0.15$ MHz whereby the pressure wave incident on diaphragm 14 is anywhere in the range from 3.21 MHz to 3.51 MHz.

To minimize the power requirements for driving crystal 16, and thereby provide an RF amplifier 18 that is of relatively low cost, maximum energy transfer must occur between transducer 16 and diaphragm 14. To these ends, (1) transducer 16 is shaped to produce a focused wave on diaphragm 14; and (2) the diaphragm has a thickness which maximizes the transfer of energy from the pressure wave incident on the diaphragm to the liquid flowing onto the diaphragm from needle 13. To achieve the focused wave, crystal 16 is shaped as a segment of a sphere which is concave with respect to diaphragm 14. The placement of crystal 16 relative to the parallel faces of diaphragm 14 and the curvature of the crystal are such that the pressure wave derived from the crystal is focused on the diaphragm; in other words, crystal 16 is spaced from diaphragm 14 by a distance roughly equal to the crystal radius of curvature. Energy transfer from crystal 16 to diaphragm 14 is enhanced by propagating the pressure wave from crystal 16 through a liquid medium continuously circulated through chamber 24, between diaphragm 14 and crystal 16.

Efficiency is also enhanced by selecting the thickness of diaphragm 14 to be approximately one-half of the wave length of the pressure wave launched by crystal 16 toward diaphragm 14. Because the pressure wave incident on diaphragm 14 is focused so that part of it propagates through the diaphragm at an incident angle relative to the diaphragm parallel faces, the wave path through the diaphragm from crystal 16 is longer than that of a wave path perpendicular to the surface of the diaphragm. Thereby the diaphragm thickness is slightly less than one-half of the wave length of the ultrasonic pressure wave propagating through it. The diaphragm thickness must of course be selected for the wave length of the pressure wave through the glass diaphragm material, rather than through air or the liquid between crystal 16 and diaphragm 14. This thickness of diaphragm 14 enables the wave fronts which are reflected from the parallel, opposite faces of diaphragm 14 to destructively interfere with each other and maximizes resonant pressure wave buildup in diaphragm 14. Thus the face of the diaphragm on which liquid flowing through needle 13 is incident receives maximum acceleration.

The liquid, preferably water, flowing by way of conduit 26 through chamber 24, cools crystal 16 and diaphragm 14. The recirculating liquid, prior to entering chamber 24, is degassified in degassification chamber 25 which may be a simple tee with an open vertical branch. The liquid flowing through chamber 24 exits by way of conduit 27 and is pressurized by pump 28, prior to being coupled back to degassifier chamber 25 by way of conduit 29. By using recirculated, degassified liquid in chamber 24, the tendency for bubbles to form in the liquid pressure wave propagation medium between diaphragm 14 and crystal 16 is virtually eliminated.

Thereby, focusing of the pressure wave from crystal 16 on transducer 14 is assured.

Liquid chromatography column 12 is driven in a conventional manner, for example, by way of loop injector 31 which includes sample source 32 and a pressurized liquid source that is supplied by pump 33 and conduit 34 to loop injector 31. As illustrated in greater detail in connection with FIG. 2, the liquid flowing through needle 13 from liquid chromatography column 12 flows onto diaphragm 14 in such a manner as to be surrounded by carrier gas from source 15. The liquid is nebulized when diaphragm 14 is energized by activation of crystal 16, at a pulse rate of 10 to 100 times every second. As described above, optimum nebulization is achieved when the diaphragm's vibration is pulsed on and off at a low rate, allowing a smooth bridge of liquid to be maintained on the diaphragm. The nebulized liquid-carrier gas mixture flows by way of transport tube 41, preferably made of stainless steel, to analyzer 42. Only a fraction of the liquid flowing through needle 13 is nebulized, with the remainder being removed by wick structure 43, coupled (as described in detail infra) to a drain (not shown).

In the illustrated embodiment, analyzer 42 is a flame photometric detector 44 located in gas chromatography oven 45. Typically, oven 45 is maintained at a temperature of 150° C. Flame photometric detector 44 includes a photomultiplier 46 for supplying an electric signal via lead 48 to recorder 47.

Detailed consideration by reference to FIGS. 2 and 3 is now given to the construction of nebulizer 11, and in particular to the construction of diaphragm 14, needle 13 and conduit 20 through which needle 13 passes. As illustrated in FIG. 2, diaphragm 14, crystal 16 and rf input connector 17 are fixedly mounted in housing 51 so that diaphragm 14 defines an end face of the housing. Connector 17 is fixedly mounted in the face of housing 51 opposite from the face defined by diaphragm 14.

Chamber 24 and housing 51, both having a cylindrical configuration, are coaxial to the aligned centers of diaphragm 14 and crystal 16, having diameters that are transverse to the longitudinal axis of chamber 24. Connector 17 and the electric leads 52 connected between it and crystal 16 are mounted in a cylindrical air filled chamber 53. Chambers 24 and 53, having aligned longitudinal axes and equal diameters, are fixedly mounted within housing 51 by conventional mounting means (not shown). To provide a uniform temperature for the components in chambers 24 and 53, housing 51 is made of a thermal insulating material.

Chamber 24 includes outlet and inlet apertures 54 and 55 respectively, immediately adjacent diaphragm 14 and crystal 16. Apertures 54 and 55 respectively define openings of tubes 27 and 26 into chamber 24. By positioning apertures 54 and 55 in the stated locations, a continuous substantially laminar liquid flow path is provided between conduits 26 and 27 within chamber 24. Such a flow path prevents distortion of the desired focusing effect for the ultrasonic pressure waves launched by crsytal 16 into chamber 24 and onto diaphragm 14, such as would occur if bubbles and violent turbulence were present. The circulating water maintains a constant temperature of piezoelectric transducer 16, and hence a constant resonant frequency. Housing 51 includes openings 57 and 58 through which tubes 26 and 27 respectively extend.

The liquid to be analyzed, typically output from a liquid chromatograph, is fed to diaphragm 14 through a vertical hollow needle 13. Needle 13 has a small diameter to limit the volume of liquid whose components might be mixed in transit.

A carrier gas, typically air, flows into the nebulizing chamber via tube 20 which coaxially surrounds needle 13. Tube 20 includes opening 63 through which needle 13 extends; opening 63 is sized such that there is a tight fit between the wall thereof and needle 13; the needle is connected in a sealed manner to opening 63. The axes of needle 13 and bore 62 are coaxial so that carrier gas supplied by tube 20 through bore 61 surrounds needle 13 and the liquid flowing out of the needle. The liquid is incident on exterior planar face 64 of diaphragm 14. Interior face 65 of diaphragm 14 is also planar and extends in a plane parallel to face 64. As described supra, the thickness of glass diaphragm 14 between planar faces 64 and 65 is slightly less than one-half of the wave length of the pressure wave propagating through glass diaphragm 14.

During the time while no pressure wave is being supplied through the liquid in chamber 24 between diaphragm 14 and crystal 16, the diaphragm is in a relaxed state, resulting in the situation illustrated in FIG. 3. In FIG. 3, needle 13 is illustrated as being configured and positioned relative to exterior face 64 such that the liquid flowing through the needle forms a bridge 65 between needle tip 66 and exterior planar face 64 of diaphragm 14. Needle tip 66 is beveled so that there is a fixed gap between it and face 64, throughout the circumference of tip 66. In other words, the tip of needle 66 is planar and beveled so that the needle tip and face 64 extend in parallel plans, both inclined at 45° relative to the vertical longitudinal axis of bore 67 of needle 13 through which the liquid flows. Bore 67, in a preferred embodiment has a diameter of 0.006 inches, while a spacing of 0.002 inches subsists between face 64 and tip 66 when diaphragm 14 is in the illustrated relaxed position. The diaphragm 14 is oscillating, the time-averaged spacing has the same value. There is a dead volume of one to two microliters, i.e., the amount of liquid in bridge 65 is one to two microliters.

The liquid flowing through bore 67 and in bridge 65 wets planar face 64. Each time an ultrasonic pressure wave is incident on diaphragm 14, the diaphragm oscillates at high frequency transversely to its face 64. It is important that there be no contact between face 64 and tip 66 to preserve the mechanical integrity of needle 13 and diaphragm 14. In the preferred embodiment the ultrasonic field incident on diaphragm 14 has a power density of approximately 500 watts per square centimeter. At this power there must be no contact between diaphragm 14 and needle 13.

In response to face 64 being oscillated the liquid in bridge or film 65 is shaken in a direction generally at right angles to face 64. A portion of the liquid in bridge or film 65 is nebulized, i.e., formed into very small droplets. The size of the droplets is a function of the frequency of the ultrasonic wave, such that as the frequency increases the size of the droplets decreases. The liquid flowing through bore 67 is directed at the focal point of the ultrasonic wave on face 64 at a very low, constant flow rate due to the small diameter of bore 67. This assists in providing smooth nebulization of the liquid in film 65. The nebulized liquid mixes with the carrier gas incident on face 64, as coupled through tube 20. Activation of diaphragm 14 from the relaxed to the oscillating state at a frequency on the order of 10 to 100

Hertz assists in providing an essentially smooth, continuous flow of the droplets and carrier gas.

Transport tube 41, preferably made of stainless steel, is fixedly mounted to the outside planar face of diaphragm 14, i.e., the face removed from chamber 24, at an area removed from the center, focal point for the pressure waves from crystal 16 on the diaphragm. Tube 41 is held in situ on the exterior face of diaphragm 14, as well as the coplanar end face of housing 51.

Conduit 41 carries the aerosol to a detector 44, such as a flame photometer in an oven 42. The output signal is connected by wire 48 to a recorder 47.

In a preferred embodiment, the liquid to be nebulized is pumped at a rate of 10 to 200 microliters per minute and the droplets have a diameter of about four micrometers and are swept from face 64 by the carrier gas. By varying the amount of RF power incident on diaphragm 14, the nebulization efficiency is varied. For example, to nebulize only 10% of a liquid flow of 100 microliters per minute, the RF power is reduced; this low mass flow rate of aerosol is needed for an analyzer capable of accepting only 10 microliters per minute of liquid aerosol drops.

A relatively small percentage of the liquid flowing through bore 67 is nebulized; typically, 10% to 30%. To remove the excess, non-nebulized liquid from face 64, wick arrangement 43 is provided.

Wick arrangement 43 includes a rust-free, metal (preferably stainless steel) screen 71, resting on face 64, and cord 72, resting on screen 71. Screen 71 includes a central aperture 73 surrounding needle 13. The diameter of aperture 73 is such that bridge 65 extends to the perimeter of the aperture, whereby there is a constant flow of liquid from bore 67 to screen 71. The liquid wicked by screen 71 is drawn from the screen by cord 72, fabricated of a conventional filament, fabric type wick material. The liquid flowing through cord 72 flows to an appropriate drain by way of conduit 43. (FIG. 1)

While there has been described and illustrated one specific embodiment of the invention, it will be clear that variations in the details of the embodiment specifically illustrated and described may be made without departing from the true spirit and scope of the invention as defined in the appended claims. For example, a fraction of the effluent from a liquid chromatography column, instead of the entire output of the column, can be supplied through needle 13 to diaphragm 14. Also, a solution to be analyzed can be pumped through needle 13, or a sample can be supplied to the needle by a flow injection analysis device. The aerosol resulting from mixing of the droplets and the carrier gas can be supplied to any appropriate analyzer, such as any flame or plasma detector, or to a mass spectrometer ion source. The droplets can be desolvated or the carrier gas can be condensed prior to being supplied to a detector. The spherical piezoelectric crystal can be replaced by a flat crystal having a sonic field focused by a lens immersed in a coupling liquid located in a chamber similar to chamber 24. Instead of pulsing the transducer by sweeping its drive signal frequency across its resonant value, an amplitude modulated RF signal can be supplied to the crystal, if appropriate compensation for resonant frequency ambient conditions for the crystal is provided. The carrier gas can be derived from gas lines supplied to a flame or plasma analyzer, or the carrier gas may be a condensable vapor. The circulating water and thermally insulating body in the region between the walls of housing 51 and chamber 24 can be replaced by a coupling fluid encased in a closed thermally conducting body, that is cooled by radiation to air.

To handle liquid flow rates less than 10 microliter per minute, diaphragm 14 can be driven at a higher frequency and the system made smaller.

What is claimed is:

1. Apparatus for supplying a nebulized aerosol and a carrier gas to a chromatography analyzer comprising a nebulizer for a liquid sample, the nebulizer including a needle having an interior bore, means for supplying the liquid to the bore, the needle having an opening through which the supplied liquid in a bore can flow, a diaphragm having a surface facing the needle opening, means for vibrating the diaphragm, and a tube surrounding the needle for supplying the carrier gas in proximity to the face so that it surrounds the needle.

2. Apparatus for nebulizing a liquid to form an aerosol comprising a needle having an interior bore, means for supplying the liquid to the bore, the needle having an opening through which the supplied liquid in the bore can flow, a diaphragm having a planar surface facing the needle opening, means for activating the diaphragm to cause the planar surface to oscillate at a high frequency, the oscillations being modulated in amplitude at a low frequency, the diaphragm being spaced from the needle opening so that they do not touch but maintain a continuous bridge of the liquid between liquid inside of the bore and the planar surface, the bridge being part of a liquid film on the planar surface when the planar surface is not oscillating, the liquid in the film being at least partially nebulized when the planar surface is oscillating to form an aerosol with a flowing carrier gas, a wick on the planar surface in contact with the film for removing from the film excess amounts of the liquid not involved in forming the aerosol.

3. The apparatus of claim 2 wherein the wick includes a generally planar segment overlaying a portion of the planar surface of the diaphragm.

4. The apparatus of claim 3 wherein the wick includes a cord portion contacting the planar segment for drawing liquid in the planar segment away from the planar surface.

5. The apparatus of claim 3 wherein the generally planar wick segment includes a central cut-out region wherein the film and bridge subsist.

6. The apparatus of claim 5 wherein the needle extends into the central cut-out region.

7. Apparatus for nebulizing a liquid to form an aerosol comprising a diaphragm, means for supplying the liquid to a face of the diaphragm, means for vibrating the diaphragm to nebulize liquid supplied to the diaphragm face to an aerosol, and a wick on the diaphragm face for removing from the face excess amounts of the liquid not involved in forming an aerosol.

8. The apparatus of claim 7 wherein the wick segment includes a central cut-out region, the means for supplying and depositing the liquid on the diaphragm face being in the cut-out region.

9. The apparatus of claim 7 wherein the means for supplying includes a needle having an interior bore and a tip with an opening into the bore, the liquid flowing through the bore and opening onto the diaphragm.

10. The apparatus of claim 7 wherein the means for activating includes a resonant electric pressure wave transducer having a tendency to change resonant frequency as a function of ambient conditions, and means for applying a frequency-modulated electric wave to the transducer, the electric wave being swept across a band of frequencies, one of the frequencies causing the transducer to be activated to resonance for the ambient condition of the transducer, activation of the transducer to resonance causing the diaphragm to be driven to an oscillatory condition from a relaxed position it occupies when the transducer is not activated to resonance.

11. The apparatus of claim 7 wherein the wick includes a generally planar segment overlaying a portion of a planar surface of the diaphragm.

12. The apparatus of claim 11 wherein the wick includes a cord portion contacting the planar segment for drawing liquid in the planar segment away from the planar surface.

13. The apparatus of claim 12 wherein the diaphragm face is inclined at an acute angle to the horizontal, the cord portion of the wick being positioned below the area where the liquid is deposited on the diaphragm.

14. Apparatus for nebulizing a liquid to form an aerosol comprising:
   a needle having an interior bore with a diameter between 0.003 and 0.012 inches;
   means for supplying liquid to the bore, the needle having an open end through which the supplied liquid in the bore can flow;
   a diaphragm having a surface facing said open end with a gap therebetween of between 0.001 and 0.004 inches, whereby a continuous bridge of liquid may be maintained between said open end and said diaphragm;
   means for vibrating the diaphragm at a high frequency, said means including means for pulse modulating said vibration at a low frequency;
   and means for supplying a flow of carrier gas through a tube surrounding said needle to sweep away the particles nebulized from said diaphragm near said open end of said needle.

15. The apparatus of claim 14 wherein the tip of the needle surrounding said open end in a plane parallel to said surface such that the gap between said tip and surface is substantially uniform, the gap and bore being dimensioned so there is a mixing volume of approximately one microliter of liquid in the film.

16. The apparatus of claim 14 wherein the means for vibrating includes a resonant electric-pressure wave transducer and said means for pulse modulating said vibration includes means for sweeping the electric wave across a band of frequencies which include the range of resonant frequencies of said transducer for a range of ambient conditions whereby said diaphragm is vibrated in a pulsed manner as the frequency sweeps over the transducer resonant frequency.

17. The apparatus of claim 16 wherein the transducer is a piezoelectric crystal.

18. The apparatus of claim 17 wherein the crystal has a fundamental resonant frequency that is a subharmonic of said resonant frequency.

19. Apparatus for nebulizing a liquid to form an aerosol comprising: a diaphragm, means for supplying the liquid to a face of the diaphragm, means for vibrating the diaphragm to nebulize liquid supplied to a face of the diaphragm to an aerosol, and means for supplying a flow of carrier gas to remove said aerosol, said means for vibrating comprising a resonant electric-to-pressure-wave transducer having a tendency to change resonant frequency as a function of ambient conditions, and means for applying a high-frequency, frequency-modulated electric wave to the transducer, comprising means for sweeping the electric wave across a band of frequencies, including the range of resonant frequencies of the transducer, whereby the transducer output is pulsed to a high value as the frequency sweeps over its current resonant frequency.

20. The apparatus of claim 19 wherein the transducer is a piezoelectric crystal.

21. The apparatus of claim 20 wherein the crystal has a fundamental resonant frequency that is a subharmonic of said one frequency causing the crystal to be activated to resonance.

22. The apparatus of claim 19 in which said means for sweeping the electric wave across a band of frequencies sweeps at a frequency several orders of magnitude below the lowest frequency of said band.

23. The apparatus of claim 19 in which said means for sweeping the electric wave sweeps at a rate of the order of 100 hertz or less, while the frequencies of said band of frequencies are of the order of a megahertz or more.

* * * * *